(12) United States Patent
Sullivan et al.

(10) Patent No.: US 10,513,678 B2
(45) Date of Patent: Dec. 24, 2019

(54) SELF-CONTAINED BIOLOGICAL INDICATOR

(71) Applicant: Mesa Laboratories, Inc., Lakewood, CO (US)

(72) Inventors: John Sullivan, Greenwood Village, CO (US); Garrett Krushefski, Bozeman, MT (US); Kurtis McCauley, Belgrade, MT (US); Eric Gillitzer, Bozeman, MT (US); Nicholas Spain, Belgrade, MT (US); Connor Campbell, Bozeman, MT (US); Ren Coleman, Frederick, CO (US); Edward Morrell, Morrison, CO (US); Jimmy Wedding, Vancouver, WA (US); John Schwend, Oregon City, OR (US)

(73) Assignee: Mesa Laboratories, Inc., Lakewood, CO (US)

( * ) Notice: Subject to any disclaimer, the term of this patent is extended or adjusted under 35 U.S.C. 154(b) by 120 days.

(21) Appl. No.: 15/381,948

(22) Filed: Dec. 16, 2016

(65) Prior Publication Data

US 2017/0175071 A1    Jun. 22, 2017

Related U.S. Application Data

(60) Provisional application No. 62/268,883, filed on Dec. 17, 2015.

(51) Int. Cl.
*C12M 1/12* (2006.01)
*C12M 1/00* (2006.01)
*C12Q 1/22* (2006.01)

(52) U.S. Cl.
CPC ............ *C12M 37/06* (2013.01); *C12M 23/38* (2013.01); *C12Q 1/22* (2013.01)

(58) Field of Classification Search
CPC ..................................................... C12M 37/06
See application file for complete search history.

(56) References Cited

U.S. PATENT DOCUMENTS

| 3,661,717 A | 5/1972 | Nelson |
| 4,291,122 A | 9/1981 | Orelski |
| 4,461,837 A | 7/1984 | Karle et al. |
| 4,528,268 A | 7/1985 | Andersen et al. |
| 4,580,682 A | 4/1986 | Gorski et al. |
| 4,596,773 A | 6/1986 | Wheeler, Jr. |

(Continued)

FOREIGN PATENT DOCUMENTS

| DE | 10046429 A1 | 4/2002 |
| EP | 0152298 A2 | 8/1985 |

(Continued)

OTHER PUBLICATIONS

John R. Gillis: "510(k) Summary, Notification EZTest Steam Biological Indicator Monitor for Steam Sterilizers"; Feb. 25, 1997, pp. 27-33.

(Continued)

*Primary Examiner* — Jonathan M Hurst
(74) *Attorney, Agent, or Firm* — Breiner & Breiner, L.L.C.

(57) ABSTRACT

A SCBI useful in ambient air pressure systems is disclosed. The SCBI includes a body which serves as the culture tube, a glass media ampoule, an inoculated stainless steel disc positioned on the top of the glass media ampoule so that the spores are close to the top/opening of the SCBI, filter paper on the top of the body and overlying the disc, and a cap.

9 Claims, 6 Drawing Sheets

(56) References Cited

U.S. PATENT DOCUMENTS

| | | | |
|---|---|---|---|
| 4,717,661 A | 1/1988 | McCormick et al. |
| 4,732,850 A | 3/1988 | Brown et al. |
| 4,741,437 A | 5/1988 | Gorski et al. |
| 4,743,537 A | 5/1988 | McCormick et al. |
| 4,883,641 A | 11/1989 | Wicks et al. |
| 4,885,253 A | 12/1989 | Kralovic |
| 5,223,401 A | 6/1993 | Foltz et al. |
| 5,498,526 A | 3/1996 | Caputo et al. |
| 5,739,004 A | 4/1998 | Woodson |
| 5,770,393 A | 6/1998 | Dalmasso et al. |
| 5,856,118 A | 1/1999 | Dalmasso |
| 5,856,172 A | 1/1999 | Greenwood et al. |
| 6,352,837 B1 | 3/2002 | Witcher |
| 6,436,659 B1 | 8/2002 | Hui et al. |
| 7,129,080 B2 | 10/2006 | Antloga et al. |
| 8,043,845 B2 | 10/2011 | Franciskovich et al. |
| 8,173,418 B2 | 5/2012 | Sestak et al. |
| 8,975,067 B2 | 3/2015 | Foltz et al. |
| 8,980,622 B2 | 3/2015 | Smith et al. |
| 2013/0210048 A1 | 8/2013 | Chandrapati et al. |
| 2013/0273594 A1 | 10/2013 | Ahimou et al. |

FOREIGN PATENT DOCUMENTS

| JP | 2006-158937 A | 6/2006 |
|---|---|---|
| WO | 2014133854 A1 | 9/2014 |
| WO | 2016057520 A1 | 4/2016 |

OTHER PUBLICATIONS

Jay Krishnan et al., Evaluation of a Ready to Use Biological Indicator System for Vhp Based Decontamination; 15 Pages, Canadian Science Centre for Human and Animal Health, Public Health Agency of Canada, Winnipeg, Canada.

3M Attest Rapid Readout Biological Indicators for 270 Degrees F/132 Degrees C Gravity Steam Sterilizers 1291; 2 Pages, 3M ID No. 70200586413, UPC No. 30707387140930, 3M.

Mesa BI, All Biological Indicators; 7 Pages, Mesa Labs, Inc.

Mesa BI, Apex Biological Indicators; 3 Pages, Mesa Labs, Inc.

ProSpore2 Self-Contained Biological Indicator for Steam/EtO Sterilization Cycles; 1 Page, Mesa Laboratories, Omaha Manufacturing Facility, Nebraska, Jan. 27, 2012.

ProStore2 for Steam and EO, Mesa Biological Indicators; 1 Page, Mesa Laboratories, Inc., May 29, 2012.

VERIFY Dual Species Self-Contained Biological Indicators; 2 Pages, STERIS Corporation.

D. Gordon et al: Article—Implications of paper vs stainless steel biological indicator substrates for formaldehyde gas decontamination; Journal of Applied Microbiology, 110, pp. 455-462, 2010,the Society for Applied Microbiology.

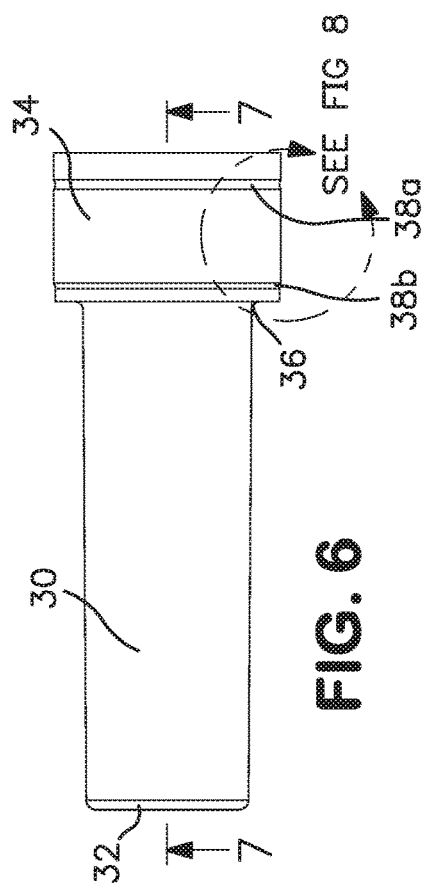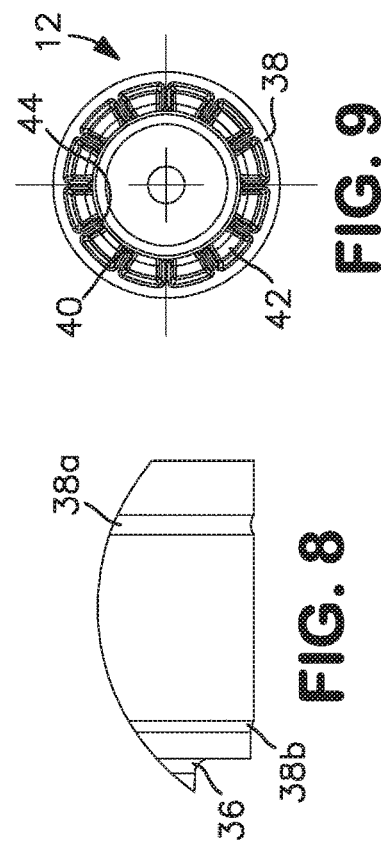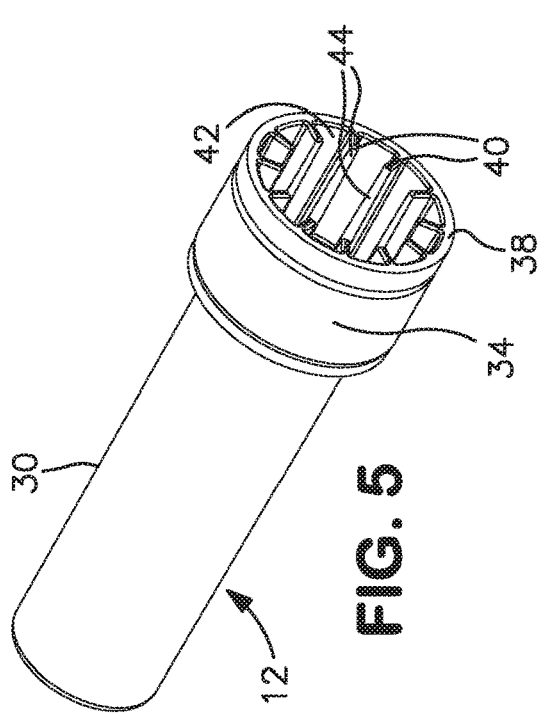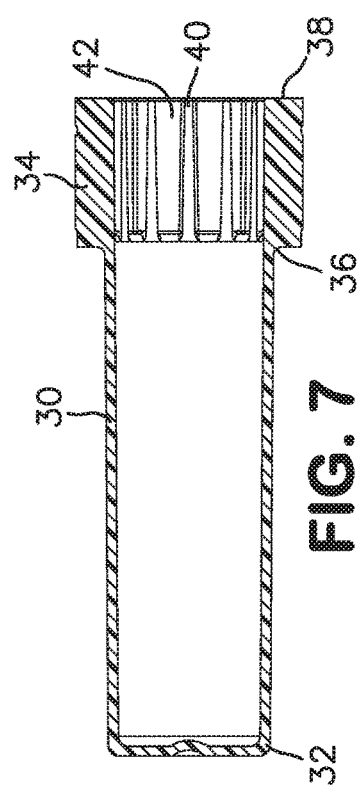

SELF-CONTAINED BIOLOGICAL INDICATOR

RELATED APPLICATION

This application claims benefit of U.S. Provisional Application Ser. No. 62/268,883, filed Dec. 17, 2015, entitled "Self-Contained Biological Indicator," and which is incorporated herein by reference in its entirety.

FIELD OF THE INVENTION

The present invention relates to biological indicators (BI) for determining the effectiveness of a sterilization and/or decontamination cycle and methods of use thereof. More particularly, the invention is directed to a self-contained biological indicator (SCBI), for use in monitoring the sterilization/decontamination of isolator systems.

BACKGROUND OF THE INVENTION

The use of BIs for verifying the effectiveness of a sterilization or decontamination cycle or process in healthcare, pharmaceutical, food processing and related fields is known. Generally, certain sterilization processes are used which include a pre-vacuum process to remove all of the ambient air from the sterilization chamber. Such processes are used for, among other things, medical instruments. In this process, the sterilization chamber is evacuated of all ambient air. This allows the sterilant to more readily reach all parts of the load including the interior of a SCBI.

Another type of sterilization or decontamination process uses an isolator which sterilization/decontamination chamber may vary in size from a few feet to a long tunnel. Such isolators do not remove all of the ambient air and are used for sterilizing or decontaminating the interior of the isolator, including all furniture such as filling lines, assembly lines, etc. The isolators may include covered openings for inserting or removing the items to be aseptically filled and/or assembled. BIs are primarily used in this process during cycle development and validation activities. Since these types of isolators do not remove all of the ambient air, the sterilant may not reach the inoculated carrier in certain SCBIs, e.g. where the carrier is located at the bottom or on the side of the SCBI. In such situations, the SCBI may not provide accurate results of the sterilization and/or decontamination process. Accordingly, there is a need in the industry for a SCBI for use in an ambient air isolator to provide accurate sterilization and/or decontamination results.

SUMMARY OF THE INVENTION

A primary object of the present invention is to provide SCBIs for determining the effectiveness of sterilization/decontamination cycles and methods of use thereof.

Another primary object of the present invention is to provide a SCBI useful in ambient air pressure systems. The SCBI of the present invention comprises a body which serves as the culture tube, a glass media ampoule, an inoculated stainless steel disc positioned on the top of the glass media ampoule so that the spores are close to the top/opening of the SCBI, filter paper on the top of the body and overlying the disc, and a cap.

These primary and other objects of the invention will be apparent from the following description of the preferred embodiments of the invention and from the accompanying drawings.

BRIEF DESCRIPTION OF THE DRAWINGS

The following detailed description of the specific non-limiting embodiments of the present invention can be best understood when read in conjunction with the following drawings, where like structures are indicated by like reference numbers.

Referring to the drawings:

FIG. 5 is a perspective view of the body of the SCBI of FIG. 1.

FIG. 6 is a side view of the body of FIG. 5.

FIG. 7 is a cross-section taken along line 7-7 of FIG. 6.

FIG. 8 is an enlarged view of the upper portion of the body taken at a portion of FIG. 6.

FIG. 9 is a top view of the body of the FIG. 5.

DETAILED DESCRIPTION OF THE PREFERRED EMBODIMENTS

Figure 1:
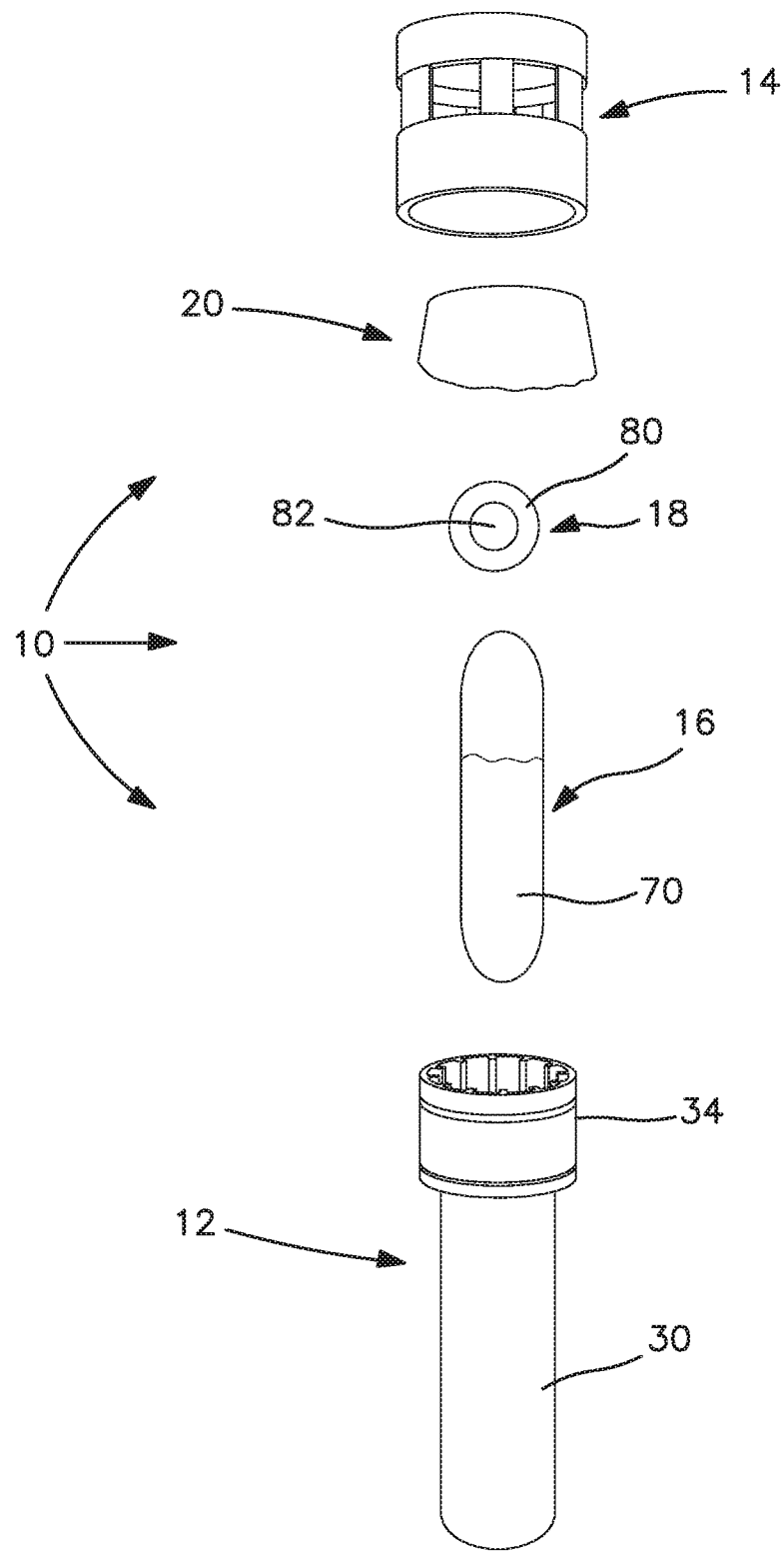
FIG. 1 is an exploded view of a SCSI of the present invention.
Figure 2:
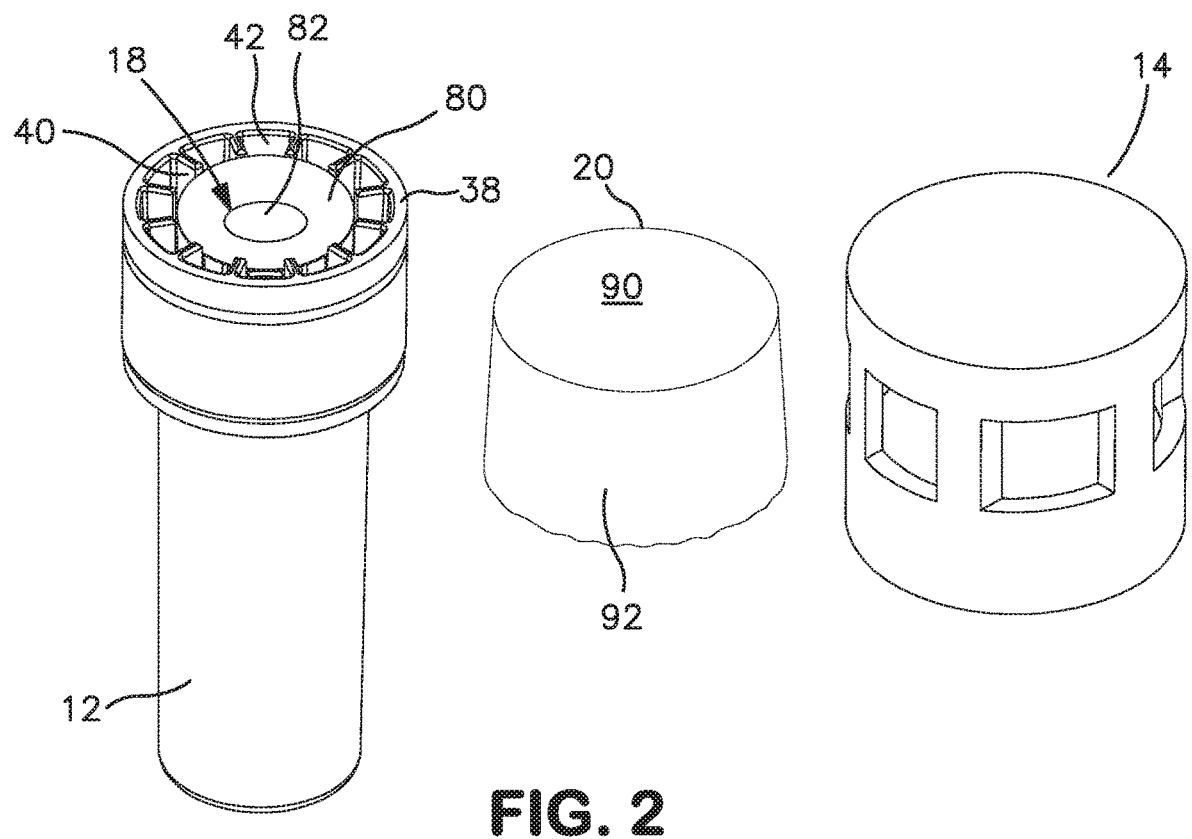
FIG. 2 is a partially assembled view of the SCBI of FIG. 1.
Figure 3:
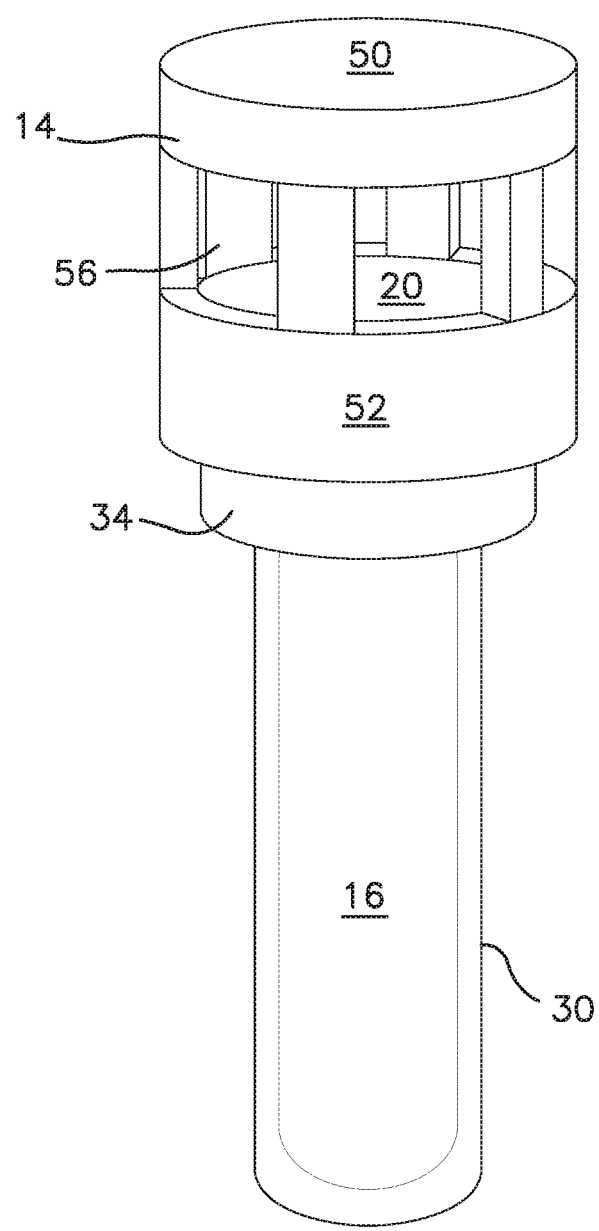
FIG. 3 is the assembled SCBI of FIG. 1 with the cap in an open position as used during a sterilization/decontamination process.
Figure 4:
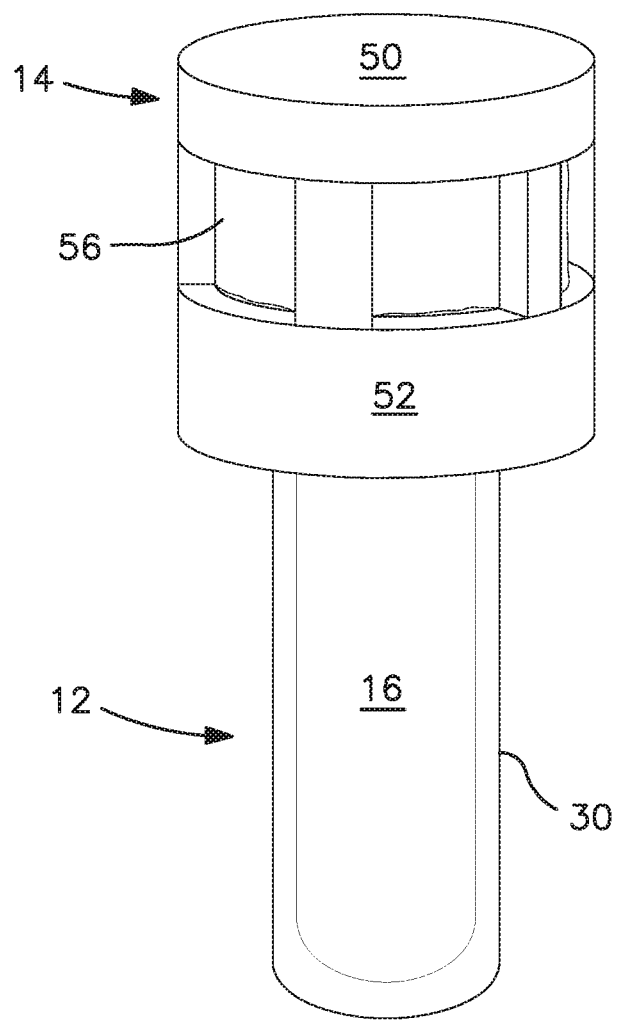
FIG. 4 is the assembled SCBI of FIG. 1 with the cap in a closed position such as after the sterilization/decontamination process and prior to incubation.
Figure 12:
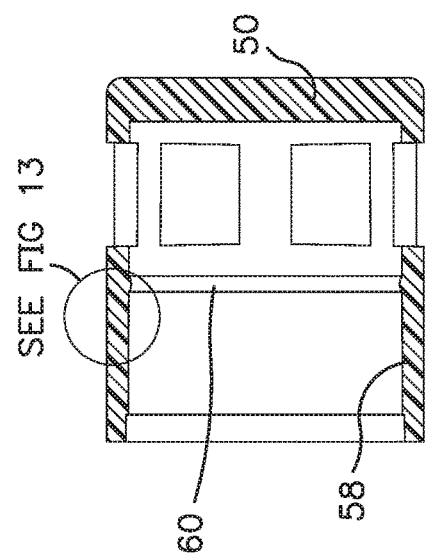
FIG. 12 is a cross-section taken along line 12-12 of FIG. 11.
Figure 14:
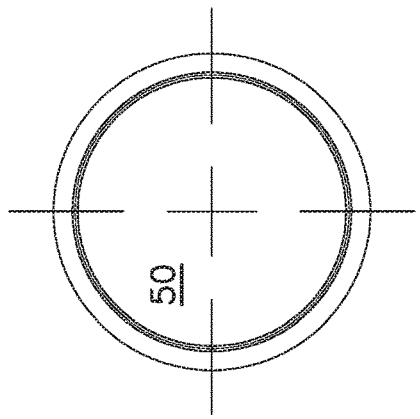
FIG. 14 is a top view of the cap of FIG. 10.
Figure 11:
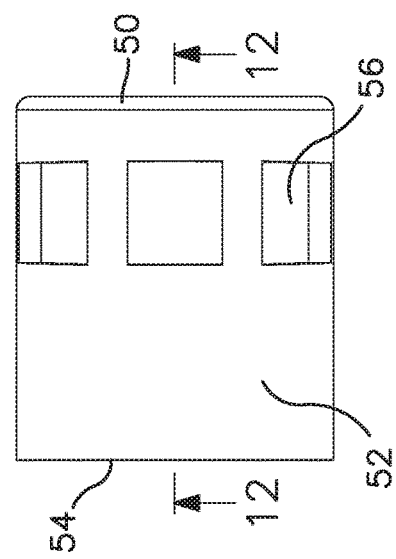
FIG. 11 is a side view of the cap of the FIG. 10.
Figure 13:
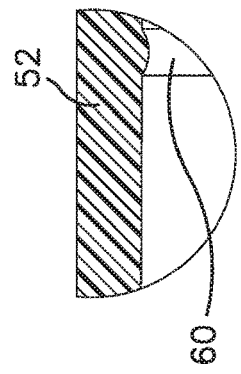
FIG. 13 is an enlarged view taken at a section of FIG. 12.
Figure 10:
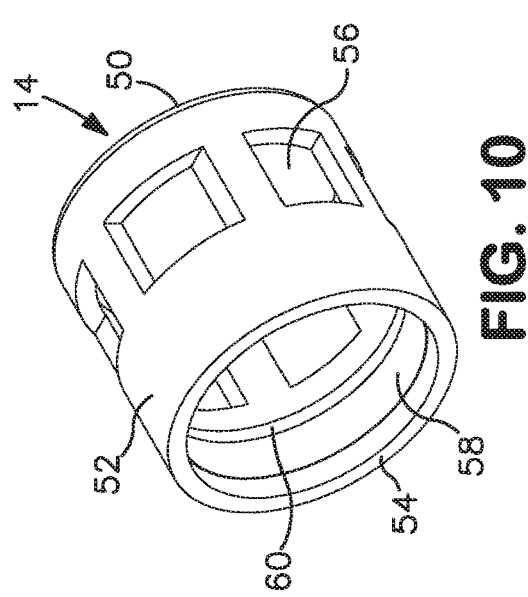
FIG. 10 is a perspective view of the cap of the SCBI of FIG. 1.

Referring to FIGS. 1-14, the present invention is directed to a SCBI 10 comprising a body 12, a cap 14, a glass media ampoule 16, an inoculated steel disc 18, and filter paper 20. The SCBI of the present invention may be used in sterilization/decontamination of items in an ambient air system such as restricted access barrier systems (RABS) such as isolators and/or room fumigation applicators using various sterilants, including hydrogen peroxide gas, chlorine dioxide gas and nitrogen dioxide gas. The SCBI is placed in an isolator chamber wherein the specific items to be sterilized/decontaminated are situated to determine the effectiveness of the sterilization/decontamination process. As seen in FIG. 3, the SCBI may be in an open position subjecting the inoculated stainless steel disc 18 to the sterilant to determine the effectiveness of the sterilization/decontamination process. After the sterilization/decontamination process, the SCSI is closed as shown in FIG. 4. The glass media ampoule 16 is opened to release a growth media. A presently preferred growth media is a proprietary growth media of Mesa Laboratories, Inc. comprising a formulated soybean casein digest culture medium containing a color indicator which turns a dramatic yellow when spores are present. Pressure is applied to the body 12 and the ampoule 16 to break the ampoule and release the growth media to the closed SCBI.

The SCBI is then placed in an incubator. After incubation, the SCBI is examined to determine whether the sterilization/decontamination process has been effective, i.e. are there any live spores.

Referring again to FIGS. 1-14, the various components of the SCBI invention will now be discussed. Body 12 includes a cylindrical side wall 30, a bottom wall 32 enclosing the body, and a collar 34 joining the cylindrical side wall 30 by shoulder 36. The collar 34 extends outwardly of the side wall 30 and is adapted to receive cap 14. Collar 34 includes an upper rim 38. Body 12 may be made of plastic such as polypropylene.

Cap 14 may be in an open position or a closed position in relation to body 12 as seen in FIGS. 3 and 4. The cap 14 is adapted to move up and down on the exterior of collar 34. On the outside wall of collar 34 there are annular protrusions 38a and 38b which serve to mate with a groove of cap 14 to hold the cap in an open position or closed position as discussed below. There are a plurality of ribs 40 in collar 34 which provide a number of functions, including providing strength and rigidity to body 12 and allowing for air flow of the sterilant down the side of the body towards the bottom of the body. A presently preferred embodiment includes twelve ribs. The ribs preferably extend outwardly from inside wall 42 between rim 38 and shoulder 36 such that the outer face 44 of the ribs is flush or even with the inside of side wall 30.

Cap 14 includes a top 50, cylindrical side wall 52 and bottom 54. The cap includes six apertures 56 through which the sterilant may enter the SCBI when in the open position. A preferred number of apertures is six to eight. Cap 14 further includes on its interior portion a skirt 58 which fits over body 12 by friction fit and is adapted to slidably move up and down the exterior wall of collar 34 of body 12. The cap includes a groove 60 which will engage protrusions 38a and 38b of body 12 to hold the cap in an open position, protrusion 38a engaging groove 60, or in a closed position, protrusion 38b engaging groove 60. Cap 14 may be made of plastic such as polypropylene.

Glass media ampoule 16 comprises an ampoule made of glass and which may be rupturable upon applying pressure to sidewall 30 and ampoule 16. The ampoule includes a growth media 70. The ampoule fits snuggly in body 12, that is, it is loose in body 12 but allows for rupture of the ampoule as described herein and seen in the Figures, and extends close to the top of collar 34 as shown, for example, in FIG. 2 and leaving sufficient space to allow disc 18 to seat on ampoule 16 as discussed below and wherein disc 18 is seated below the rim 38 of collar 34. The growth media is used when testing the efficacy of the sterilization/decontamination process, i.e. during the incubation process to determine whether there are any live spores.

The inoculated stainless steel disc 18 comprises a disc made of stainless steel, preferably a 9 millimeter stainless steel disc. The disc is dish shaped having an outer edge 80 and a central portion 82. The disc is inoculated with spores (not shown) such as *G. stearothermophilus*. A preferred disc is made by Mesa Laboratories and sold under the trademark APEX®. The disc is located on top of the glass media ampoule 16. As shown in FIG. 2, the outside diameter of the disc is of a smaller dimension then the inside diameter formed by the ribs 40 such that when ampoule 16 is broken the disc will drop down into body 12 to fully interact with the growth media. Accordingly, the spores on disc 18 are close to the top/opening of the SCBI during the sterilization/decontamination process. This ensures that the sterilant reaches the disc 18 during a sterilization/decontamination process in an ambient pressure system.

Figure 2A:
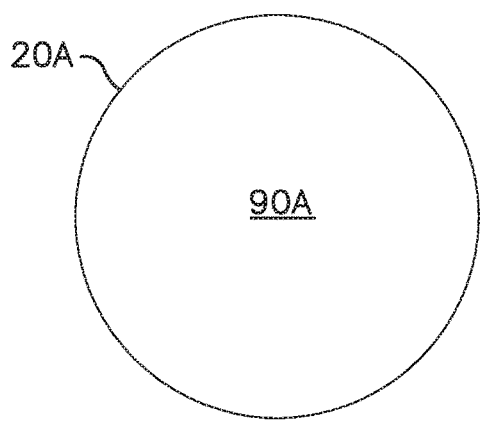
FIG. 2A is a perspective view of one embodiment of filter paper.

Filter paper 20 is located above the collar 34 and covers the inoculated stainless steel disc 18. A preferred filter paper is Tyvek® paper. The filter paper may include a top portion 90 having a side wall portion 92 which fits over the exterior wall of collar 34 of body 12. In a preferred embodiment, the filter paper 20 comprises a round planar structure 20A as shown in FIG. 2A having a top portion 90A and covers the top of the body 12 and the inoculated stainless steel disc 18.

In one preferred embodiment, the SCBI includes the following dimensions in inches: body 12 height is 1.75; collar 34 height is 0.36 and collar outside diameter is 0.602; bottom wall 30 outside diameter is 0.41 and bottom wall 30 inside diameter is 0.38; cap 14 height is 0.81 and cap outside diameter is 0.705

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

The invention claimed is:

1. A self-contained biological indicator comprising:
   a body adapted to serve as a culture tube, said body having a substantially uniform cylindrical side wall with a substantially constant diameter, a bottom wall at one end of the cylindrical side wall closing the body, a collar at the other end of the cylindrical side wall extending outwardly from the cylindrical side wall having an open end having an interior diameter greater than an interior diameter of the cylindrical side wall and adapted to receive a cap, said collar including a plurality of inwardly extending ribs;
   a cap adapted to engage said body in an open position and a closed position, said cap including a top wall and a cylindrical side wall adapted to engage said collar of said body, said cylindrical side wall including a plurality of apertures;
   a rupturable glass ampoule including a growth media in said body;
   a stainless steel disc inoculated with spores on top of said glass ampoule and adjacent said plurality of ribs; and
   a filter paper covering said stainless steel disc.

2. A self-contained biological indicator according to claim 1 wherein said plurality of inwardly extending ribs extend a horizontal length of said collar and are substantially even with an inside wall of said cylindrical side wall of said body.

3. A self-contained biological indicator according to claim 2 wherein said plurality of ribs comprise twelve ribs.

4. A self-contained biological indicator according to claim 1 wherein said plurality of ribs are adapted to allow air flow of a sterilant down the side of said body towards the bottom of said body.

5. A self-contained biological indicator according to claim 1 wherein said disc is adapted to drop down into said body when said glass ampoule is ruptured.

6. A self-contained biological indicator according to claim 1 wherein said growth media is a formulated soybean casein digest culture medium.

7. A self-contained biological indicator according to claim 1 wherein said plurality of apertures of said cylindrical side wall of said cap comprise six to eight apertures.

8. A self-contained biological indicator according to claim 1 wherein said cap includes an annular groove on the inside of said cylindrical side wall and said collar of said body includes upper and lower annular protrusions adapted to engage said annular groove to hold said cap in open and closed positions.

9. A self-contained biological indicator comprising:
a body adapted to serve as a culture tube, said body having a substantially uniform cylindrical side wall with a substantially constant diameter, a bottom wall at one end of the cylindrical side wall closing the body, a collar at the other end of the cylindrical side wall extending outwardly from the cylindrical side wall having an open end having an interior diameter greater than an interior diameter of the cylindrical side wall and adapted to receive a cap, said collar including a plurality of inwardly extending ribs wherein said plurality of inwardly extending ribs extend the horizontal length of said collar and are substantially even with the inside wall of said cylindrical side wall of said body;
a cap adapted to engage said body in an open position and a closed position, said cap including a top wall and a cylindrical side wall adapted to engage said collar of said body, said cylindrical side wall including a plurality of apertures wherein said plurality of apertures comprise six to eight apertures;
a rupturable glass ampoule including a growth media in said body wherein said growth media is a formulated soybean casein digest culture medium;
a stainless steel disc inoculated with spores and adapted to fit into said body and on top of said glass ampoule and adjacent said plurality of ribs wherein said disc is adapted to drop down into said body when said glass ampoule is ruptured; and
a filter paper covering said stainless steel disc.

* * * * *